US012781092B2

(12) United States Patent
Mountfort

(10) Patent No.: US 12,781,092 B2
(45) Date of Patent: Nov. 3, 2026

(54) METHOD OF EXTRACTION

(71) Applicant: Foresta Group Holdings Limited, Landsborough (AU)

(72) Inventor: Ramon Dudley Mountfort, Isis Central (AU)

(73) Assignee: Foresta Group Holdings Limited, Landsborough (AU)

( * ) Notice: Subject to any disclaimer, the term of this patent is extended or adjusted under 35 U.S.C. 154(b) by 761 days.

(21) Appl. No.: 18/010,303

(22) PCT Filed: Jun. 16, 2021

(86) PCT No.: PCT/AU2021/050622

§ 371 (c)(1),
(2) Date: Dec. 14, 2022

(87) PCT Pub. No.: WO2021/253083

PCT Pub. Date: Dec. 23, 2021

(65) Prior Publication Data

US 2023/0279265 A1 Sep. 7, 2023

(30) Foreign Application Priority Data

Jun. 16, 2020 (AU) ................................ 2020901996

(51) Int. Cl.
*C09F 1/02* (2006.01)
*B01D 11/00* (2006.01)
(Continued)

(52) U.S. Cl.
CPC .............. *C09F 1/02* (2013.01); *B01D 11/028* (2013.01); *B01D 11/0288* (2013.01); (Continued)

(58) Field of Classification Search
CPC ..... C09F 1/02; C09F 1/04; C09F 3/00; B01D 11/028; B01D 11/0288; B01D 11/0296; B01D 2011/002; C07C 7/08; C08L 93/04
(Continued)

(56) References Cited

U.S. PATENT DOCUMENTS 915,400 A * 3/1909 Yaryan ...................... C09F 1/00 585/947
1,059,261 A 4/1913 Bashlin
(Continued)

FOREIGN PATENT DOCUMENTS

CN 101486878 A 7/2009
CN 102634282 A 8/2012
(Continued)

OTHER PUBLICATIONS

International Bureau, International Search Report and Written Opinion issued in International Patent Application No. PCT/AU2021/050622, mailed on Aug. 18, 2021.

*Primary Examiner* — David T Karst
(74) *Attorney, Agent, or Firm* — Leydig, Voit & Mayer, Ltd.

(57) ABSTRACT

The present disclosure relates to methods and an apparatus for extracting terpenes and rosin from resinous wood with an agent that comprises, consists or consists essentially of a terpene to thereby extract the rosin and/or terpene fractions from the resinous wood. The apparatus for extracting rosin and/or terpene fractions comprises a treatment chamber for treating the resinous wood with the agent. The treatment chamber is in communication with a distillation chamber for separating the rosin and terpene fractions extracted from the resinous wood.

20 Claims, 2 Drawing Sheets

(51) Int. Cl.

| | |
|---|---|
| ***B01D 11/02*** | (2006.01) |
| ***C07C 7/08*** | (2006.01) |
| ***C08L 93/04*** | (2006.01) |
| ***C09F 1/04*** | (2006.01) |
| ***C09F 3/00*** | (2006.01) |

(52) U.S. Cl.
CPC ............ *B01D 11/0296* (2013.01); *C07C 7/08* (2013.01); *C08L 93/04* (2013.01); *C09F 1/04* (2013.01); *C09F 3/00* (2013.01); *B01D 2011/002* (2013.01)

(58) Field of Classification Search
USPC .......................................................... 530/228
See application file for complete search history.

(56) References Cited

U.S. PATENT DOCUMENTS

| | | | | |
|---|---|---|---|---|
| 1,252,058 A | | 1/1918 | Teeple | |
| 1,465,565 A | | 8/1923 | Scheller | |
| 2,757,169 A | * | 7/1956 | Cook, Jr. | C09F 1/00 530/202 |
| 4,308,200 A | | 12/1981 | Fremont | |
| 4,906,733 A | * | 3/1990 | Kodama | C09F 1/00 530/223 |
| 2003/0087789 A1 | | 5/2003 | Scheffler | |
| 2015/0080566 A1 | | 3/2015 | Wiesbeck | |
| 2019/0256795 A1 | | 8/2019 | Sturm et al. | |

FOREIGN PATENT DOCUMENTS

| | | | |
|---|---|---|---|
| CN | 105778764 | A | 7/2016 |
| CN | 110408324 | A | 11/2019 |
| GB | 1014678 | A | 12/1965 |
| JP | 2001-504752 | A | 4/2001 |
| JP | 2004-519411 | A | 7/2004 |
| KR | 10-1230388 | B1 | 2/2013 |
| WO | WO 2005/023948 | A1 | 3/2005 |
| WO | WO 2016/004481 | A1 | 1/2016 |
| WO | WO 2016/004482 | A1 | 1/2016 |

* cited by examiner

A

B

METHOD OF EXTRACTION

CROSS-REFERENCE TO RELATED APPLICATIONS

The present application is the U.S. National Stage of International Patent Application No. PCT/AU2021/050622, filed Jun. 16, 2021, which claims priority to Australian Provisional Patent Application No. 2020901996 filed on Jun. 16, 2020, the contents of which are incorporated herein by reference in their entirety.

TECHNICAL FIELD

THIS DISCLOSURE relates to methods and an apparatus for extracting terpenes and rosin from resinous wood.

BACKGROUND

There are three acknowledged commercial sources of rosin (or colophony) and terpenes (or turpentine). These include chemical pulping (i.e., tall oil and CST-derived rosin and terpene), the manual or semi manual tapping of live trees (i.e., gum rosin and gum turpentine) and solvent extraction (i.e., wood rosin and wood turpentine).

Chemical pulping typically uses strong bases and acids to break down the wood and the rosins and terpenes are given off as a by-product of this process. In doing so, the rosins and terpenes derived by this process can contain significant levels of contaminants (e.g., sulphide and sulphate compounds) from the pulping process that must then be removed through various filtering and distillation processes. As such, complete removal of trace chemicals or contaminants from such rosin and terpenes is generally not commercially viable. Additionally, complete recovery of the available rosin and terpenes in the wood is not possible with the chemical pulping process due to their degradation to, for example, pitch and other compounds therein. Chemical pulping as a means of extracting pine chemicals can further present a number of negative environmental impacts, such as the discharge of heavy metals and toxic compounds into the environment.

Gum tapping is done using various methods of mechanical cutting, scraping, wounding or drilling a living tree. To obtain commercially viable yields from this process, however, chemical stimulants are typically used to ensure that the wound continues to bleed and give off its extractives. These stimulants can include acids and hormones such as ethephon and sulphuric acid. Such chemicals can adversely alter the physical composition of the resultant rosin and terpenes. By way of example, acid can cause the terpenes to polymerise, resulting in higher concentrations of diterpenes and triterpenes than exist naturally in the tree. These terpene polymers are also less sought after than monoterpenes, such as α- and β-pinene. As such, the process of gum tapping typically requires a washing step to remove the added chemicals with trace chemicals often still remaining. This washing step also creates a waste stream with the contaminated water commonly being salt water.

Wood rosin and terpenes are generally extracted using tree stumps and a solvent. The solvent is typically hexane, methyl ethyl ketone or another hydrocarbon. The process is to wash the wood in the solvent and subsequently distil the concentrate produced into the solvent, rosin and terpenes. Notwithstanding this, the resultant wood rosin and terpenes from this solvent extraction process can still contain significant traces of the solvent and other contaminants. Additionally, wood rosin produced by this process generally requires further decolourisation processing, which can adversely affect yields and modify the rosin.

Accordingly, improved methods for extracting rosin and terpenes from resinous wood that may be less damaging to these end products and/or may be more environmentally friendly are required.

SUMMARY

The present disclosure is predicated in part on the surprising discovery that treating resinous wood with an agent that is or includes a terpene-based solvent can result in more efficient and improved extraction of terpenes and rosin from such wood with reduced levels of contamination by unwanted chemicals.

In a first aspect, the disclosure provides a method for extracting rosin and/or terpene fractions from a resinous wood, said method including the step of treating the resinous wood with an agent that comprises, consists or consists essentially of a terpene to thereby extract the rosin and/or terpene fractions from the resinous wood.

Suitably, the present method further includes the initial step of at least partly subdividing, such as chipping, the resinous wood prior to treatment with the agent. In some examples, a period of time between the initial step of subdividing the resinous wood and treating the resinous wood with the agent may be no more than about 12 hours, no more than about 8 hours, no more than about 4 hours, no more than about 2 hours or no more than about 1 hour.

Suitably, the current method further includes the step of separating the rosin fraction and the terpene fraction extracted from the resinous wood. In some examples, separating the rosin fraction and the terpene fraction is performed at least in part by distillation to produce a distillate that comprises, consists essentially of or consists of the terpene fraction and a residual stream that comprises, consists essentially of or consists of the rosin fraction. In certain examples, the present method further includes the step of separating or recovering the terpene fraction from the distillate.

In particular examples, the present method includes the subsequent step of heating, such as steam treating, the resinous wood treated with the agent to at least partly remove residual portions of the agent and/or the terpene fraction therefrom.

Suitably, the step of treating the resinous wood with the agent is performed for a period of time and under conditions sufficient or suitable to extract the rosin and/or terpene fractions from the resinous wood. In some examples, the step of treating the resinous wood with the agent is performed for a period of time from about 15 minutes to about 120 minutes. In various examples, the step of treating the resinous wood with the agent is performed at a temperature from about 75° C. to about 155° C. In some examples, the step of treating the resinous wood with the agent is performed at a pressure of about 10 psi to about 75 psi.

Suitably, the resinous wood is contacted or treated with the agent in a counter-current or counter-flow manner.

In particular examples, the rosin and/or the terpene fractions extracted from the resinous wood are substantially free of contaminants.

In certain examples, the agent is at least partly derived from the terpene fraction extracted from the resinous wood. In this regard, the present method may include the further step of recycling the terpene fraction extracted from the resinous wood and/or the agent for use in the treatment step.

In some examples, the resinous wood is substantially untreated prior to treatment with the agent.

In various examples, the resinous wood is at least partly derived from or comprises one or more resinous wood logs and/or stumps.

In a second aspect, the disclosure provides a terpene fraction produced according to the method of the first aspect.

In some examples of the above aspects, the terpene fraction comprises at least about 65%, at least about 70%, at least about 75% or at least about 80% pinenes by weight of the terpene fraction.

In various examples of the above aspects, wherein the terpene fraction is substantially free of contaminants.

In particular examples of the above aspects, the terpene fraction comprises less than about 25%, less than about 10%, less than about 5%, less than about 2.5% or less than about 1% terpene polymers, such as diterpenes and triterpenes, by weight of the terpene fraction.

In certain examples of the above aspects, the terpene fraction comprises less than about 10%, less than about 5%, less than about 2.5%, less than about 1% or less than about 0.5% synthetic pine oil by weight of the terpene fraction.

In a third aspect, the disclosure provides a rosin fraction produced according to the method of the first aspect.

In certain examples of the above aspects, the rosin fraction has a Gardner colour number of no more than about 8, no more than about 5 or no more than about 3.

In various examples of the above aspects, the rosin fraction is substantially free of contaminants.

In particular examples of the above aspects, the rosin fraction has an acid value between about 160 to about 175.

In some examples of the above aspects, the rosin fraction comprises an abietic acid content in the range from about 15% to about 35%, about 15% to about 25% or about 15% to about 20% by weight of the rosin fraction.

In a fourth aspect, the disclosure provides an isolated terpene fraction that is or comprises one or more of:

(a) at least about 65%, at least about 70%, at least about 75% or at least about 80% pinenes by weight of the isolated terpene fraction;
(b) substantially free of contaminants;
(c) less than about 25%, less than about 10%, less than about 5%, less than about 2.5% or less than about 1% terpene polymers by weight of the isolated terpene fraction; and
(d) less than about 10%, less than about 5%, less than about 2.5%, less than about 1% or less than about 0.5% synthetic pine oil by weight of the isolated terpene fraction.

In a fifth aspect, the disclosure provides an isolated rosin fraction that is or comprises one or more of:

(a) a Gardner colour number of no more than about 8, no more than about 5 or no more than about 3;
(b) substantially free of contaminants;
(c) an acid value between about 160 to about 175; and
(d) an abietic acid content in the range from about 15% to about 35%, about 15% to about 25% or about 15% to about 20% by weight of the isolated rosin fraction.

In a sixth aspect, the disclosure provides a method of making a polymer, said method including the step of treating a rosin fraction and/or a terpene fraction produced according to the method of the first aspect to thereby make the polymer.

In a seventh aspect, the disclosure relates to a polymer produced according to the method of the sixth aspect.

In an eighth aspect, the disclosure provides a method of making an ester, said method including the step of treating a rosin fraction and/or a terpene fraction produced according to the method of the first aspect to thereby make the ester.

In a ninth aspect, the disclosure relates to an ester produced according to the method of the eighth aspect.

In a tenth aspect, the disclosure provides an apparatus for extracting rosin and/or terpene fractions from a resinous wood comprising: a treatment chamber for treating the resinous wood with an agent that comprises, consists or consists essentially of a terpene.

In some examples, the treatment chamber is or comprises a counter-current extractor.

In certain examples, the apparatus further comprises a distillation chamber in communication with the treatment chamber, the distillation chamber for separating the rosin and terpene fractions extracted from the resinous wood.

In various examples, the apparatus further comprises a desolventiser in communication with the treatment chamber, the desolventiser capable of heating, such as by steam or heating oils, treating, the resinous wood treated with the agent so as to at least partly remove residual portions of the agent and/or the terpene fraction therefrom.

In particular examples, the apparatus further comprises a separator, such as a condenser, in communication with the distillation chamber, the separator for separating the terpene fraction from a distillate produced by the distillation chamber.

In some examples, the apparatus further comprises a scrubbing device.

Suitably, the apparatus is for use in the method of the first aspect.

Throughout this specification, unless otherwise indicated, "comprise", "comprises" and "comprising" are used inclusively rather than exclusively, so that a stated integer or group of integers may include one or more other non-stated integers or groups of integers.

Conversely, the terms "consist", "consists" and "consisting" are used exclusively, such that a stated integer or group of integers are required or mandatory, and no other integers may be present. The phrase "consisting essentially of" indicates that a stated integer or group of integers are required or mandatory, but that other elements that do not interfere with or contribute to the activity or action of the stated integer or group of integers are optional.

It will also be appreciated that the indefinite articles "a" and "an" are not to be read as singular indefinite articles or as otherwise excluding more than one or more than a single subject to which the indefinite article refers. For example, "a" protein includes one protein, one or more proteins or a plurality of proteins.

As used in this specification, the term "about" refers to a variation or tolerance in a stated amount, concentration, ratio or proportion. The extent of such tolerances and variances are well understood by persons skilled in the art. Typically, such tolerances and variances do not compromise the structure, function and/or implementation of the apparatuses and methods described herein. Preferably, "about" is defined as being no more than 10%, 5%, 2% or 1% above or below a stated amount, concentration, ratio or proportion.

BRIEF DESCRIPTION OF THE DRAWINGS

By way of example only, an embodiment of the disclosure is described more fully hereinafter with reference to the accompanying drawing, in which:—

DETAILED DESCRIPTION

Figure 1:
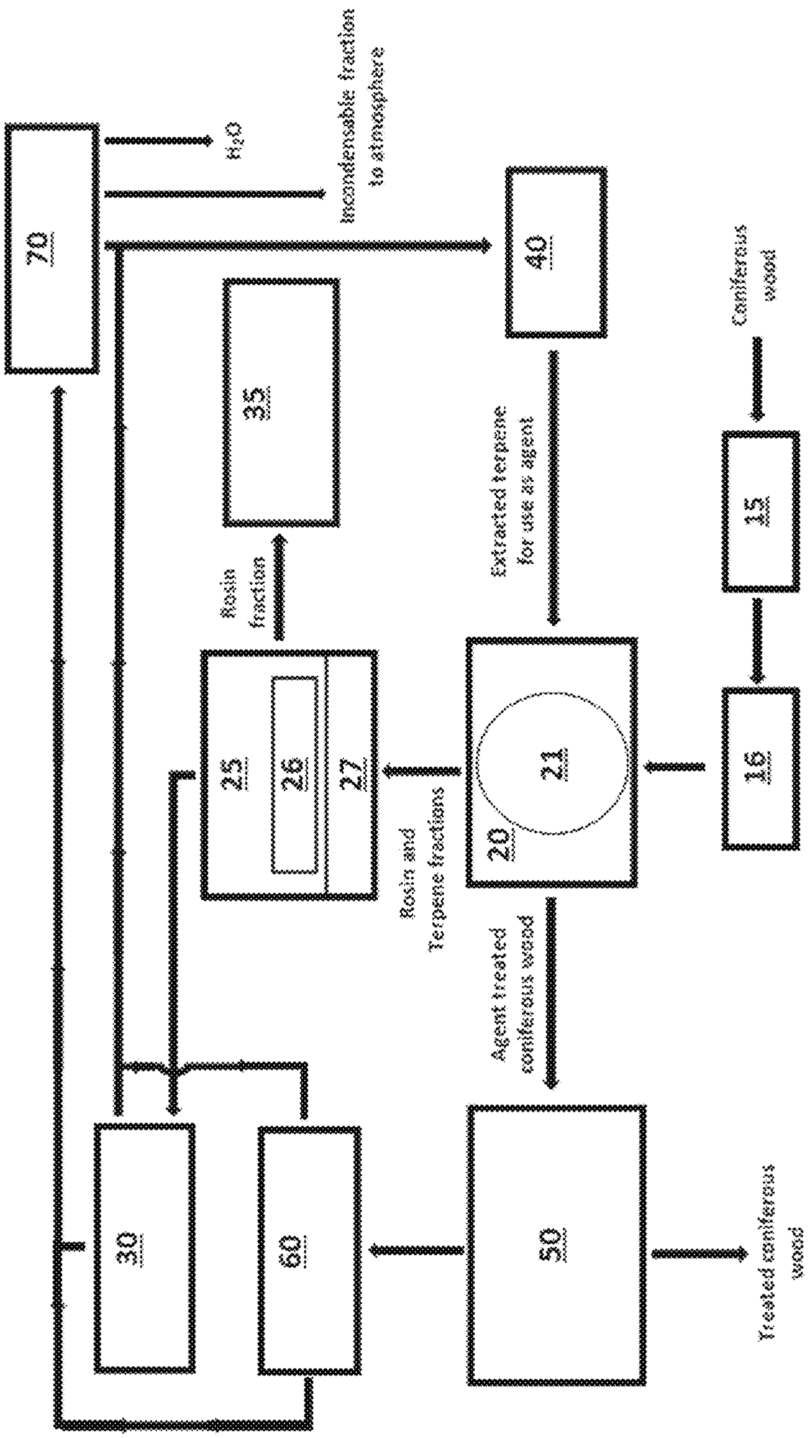
FIG. 1 is a schematic of an apparatus or system according to a particular embodiment of the disclosure.

The present disclosure arises, in part, from the identification of novel methods of extracting rosin and terpenes from resinous wood. In particular, these novel methods provide for the production of improved rosin and terpene fractions that exhibit no or minimal contaminants or trace chemicals and are hence more amenable for downstream use. Additionally, the methods described herein typically have lower capital and operational costs, and/or may be more efficient, and/or may demonstrate improved yields and/or may be more environmentally friendly than those previously described in the art.

The present disclosure provides a non-destructive solvent-based extraction method for the production of rosin and terpenes sourced from resinous wood using a self-sustaining and self-generating solvent, namely the terpenes that exist naturally in the resinous wood. By virtue of this arrangement, the present extraction method can advantageously produce rosin and terpene fractions that have no or substantially no residues of any reagents or trace chemicals, such as those typically found for existing rosin and terpene production methods. Solvent extraction by the method of the disclosure can also provide improved efficiency, with extraction of rosin and terpene fractions taking as little as half the time as other solvent extraction processes known in the art (e.g., only about 30 min to about 45 min). This improved efficiency minimises any chemical and/or physical changes in the rosin and terpene fractions, such as oxidation and terpene polymerisation, which can be detrimental to the value and utility thereof. Furthermore, this can minimise the variation between production batches with rosin and terpene fractions derived by the method of the disclosure typically demonstrating the same or within 1% variability of chemical composition between batches versus other prior art methods which can demonstrate greater variability of up to 10% or more between batches. The extraction process is also typically simpler than prior art methods due to a single separation step of the rosin fraction from the terpene fraction with no requirement for the removal of a further solvent. In this regard, the solvent extraction methods of the prior art typically involve a two-step process in which the resinous material is removed from the wood by solvent treatment and then any retained solvent is recovered from the treated wood by steaming (see, e.g., Beglinger, E. (1958); Distillation of resinous wood). Waste streams are also minimised with no requirement to burn hazardous chemicals or discharge salty contaminated water.

In one aspect, the disclosure resides in a method for extracting a rosin fraction and/or a terpene fraction, including components or derivatives thereof, from a resinous wood, said method including the step of treating the resinous wood with an agent that comprises, consists or consists essentially of a terpene to thereby extract the rosin and/or terpene fractions from the resinous wood.

As used herein, the term "rosin" broadly refers to a resin obtained from different species of resinous trees, such as coniferous or softwood trees. Whilst the composition of rosins can vary somewhat according to their source, usually they comprise, as a major component, resin acids such as unsaturated mono-carboxylic acids, including components or derivatives thereof. In this regard, the proportion of different resin acids in rosin can vary according to the softwood or coniferous species from which the rosin was obtained. By way of example, the rosin may contain from 85 to 95% of resin acids. In general, rosin primarily contains abietic acid (e.g., from 50% to 80%), and to a lesser extent dihydroabietic acid (e.g., from 5% to 30%) and pimaric acid (e.g., from 5% to 30%). Rosin may also include isopromic acid, palustric acid, and neoabietic acid.

The terms "terpene" and "turpentine" are used interchangeably herein and refer to the large and diverse class of organic compounds produced by a variety of plants, particularly conifers. As will be appreciated, the main components of terpene or turpentine are unsaturated hydrocarbon monoterpenes, such as $\alpha$-pinene, $\beta$-pinene and 3-carene.

Broadly, "resinous wood" refers to wood that contains a portion of resin. Resinous wood is generally associated with softer wood species, like pine, that secrete resin as protection mechanism against parasites and disease, but may also include resinous hardwood species, such as teak, agarwood and acacia. In some examples, the resinous wood contains a terpene fraction. In other examples, the resinous wood contains a rosin fraction. In further examples, the resinous wood contains a terpene fraction and a rosin fraction.

In particular examples, the resinous wood comprises, consists of or consists essentially of a coniferous wood. Thus, any reference herein to "resinous wood" may be understood to encompass coniferous wood. Accordingly, any description herein of any aspect, example, embodiment or feature of the present disclosure which is described in terms of "resinous wood" is to be understood to apply equally to coniferous wood. As generally used herein, the term "coniferous wood" refers to, for example, fibrous masses obtained from the wood of coniferous trees (i.e., gymnosperms), such as varieties of fir, larch, spruce, cedar, cypress, yew and pine. Non-limiting examples include Caribbean Pine, Slash pine, Colorado spruce, balsam fir, Douglas fir, incense pine, Elliot pine, prickly spruce, Banks pine, *Radiata* pine, white spruce, broadly twisted pine and *sequoia.*

The resinous wood can be derived from a single type or species of tree or conifer or a combination thereof (e.g., 1, 2, 3, 4, 5 etc types or species) and/or can be non-modified and/or modified. The resinous wood can also be transgenic (i.e., genetically modified) and derived from any portion of a tree or plant, such as branches, logs, roots and stumps.

In some examples, the resinous wood is substantially derived from logs. As the skilled person will appreciate that term "log" is to be used in a broad sense and typically refers to a harvested tree unit, which may be at least partly debarked or retain all or substantially all of its bark.

In other examples, the resinous wood is substantially derived from stumps. Generally, the term "stump" refers to the remainder of a felled or harvested tree (e.g., a tree base), which at least in the area of the roots, extends into the ground. The stumps may be substantially debarked or retain some or substantially all of their bark. Similarly, the stumps may have a portion or substantially all of their roots removed prior to use in the method of the present disclosure.

For the present disclosure, the resinous wood may have been processed by a processor, such as a tree harvesting or stump removal operation, prior to treatment with the agent.

It is envisaged that the present method may further include the initial step of harvesting the resinous wood, such as from a plantation or the like. In particular examples, the period of time between harvesting the resinous wood and treating the resinous wood with the agent is no more than about 12 weeks (e.g., about 12, 11, 10, 9, 8, 7, 6, 5, 4, 3, 2, 1 week or any range therein), no more than about 4 weeks, no more than about 2 weeks or no more than about 1 week.

To this end, the inventors have found that this time frame advantageously minimises loss of the terpene fraction to evaporation thereby maximising yield thereof and minimising any effects of oxidation of the rosin fraction in the resinous wood which can adversely affect its colour and reactivity. Preferably, the resinous wood undergoes little or no further processing or treatment after harvesting and prior to treatment with the agent (i.e., the resinous wood is essentially in its natural state).

As used herein, "treating" or "treatment" may refer to, for example, contacting, soaking, steam impregnating, spraying, suspending, immersing, saturating, dipping, wetting, rinsing, atmospheric mechanical refining, impregnating, washing, submerging, and/or any variation and/or combination thereof.

As will be understood by the skilled person, the step of treating the resinous wood may simply comprise passage of the resinous wood through a bath containing the agent. In other examples, the step of treating the resinous wood comprises passage of the resinous wood through a batch vessel, wherein the batch vessel recirculates the agent.

In certain examples, the resinous wood is contacted or treated in a counter-current or counter-flow manner with the agent. The term "counter-flow" or "counter-current" is understood to mean that the resinous wood being treated in a treatment chamber or the like generally flow, or are conveyed, in one direction, whereas the agent and/or the terpene/rosin fractions extracted by the treatment process flow in an opposite direction. By way of example, the step of treating the resinous wood comprises passage of the resinous wood through a rotary extractor, a loop type extractor, a drag chain extractor and/or a continuous belt extractor.

Suitably, the step of treating the resinous wood with the agent is performed for a period of time and under conditions sufficient or suitable to extract the rosin and/or terpene fractions from the resinous wood.

To this end, the treatment step, at least partly, is suitably carried out at a temperature from about 60° C. to about 155° C., or any range therein, such as, but not limited to, about 70° C. to about 140° C. or about 75° C. to about 130° C. Suitably, the treatment temperature is higher than the melting point of the rosin fraction at the pressure at which the treatment step is to be performed (e.g., greater than about 73° C. at atmospheric pressure). Similarly, the treatment temperature is suitably lower than the boiling point of the terpene fraction (e.g., pinenes) at the pressure at which the treatment step is to be performed (e.g., less than about 155-156° C. at atmospheric pressure). In particular examples, the treatment step is carried out at a temperature of about 60° C., 61° C., 62° C., 63° C., 64° C., 65° C., 66° C., 67° C., 68° C., 69° C., 70° C., 71° C., 72° C., 73° C. 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., 130° C., 131° C., 132° C., 133° C., 134° C., 135° C., 136° C., 137° C., 138° C., 139° C., 140° C., 141° C., 142° C., 143° C., 144° C., 145° C., 146° C., 147° C., 148° C., 149° C., 150° C., 151° C., 152° C., 153° C., 154° C., 155° C. or any range therein. In particular examples, the treatment step is carried out at a temperature from about 75° C. to about 155° C.

Furthermore, the treatment step can be performed or carried out for a period of time from about 5 minutes to about 240 minutes or any range therein, such as, but not limited to, about 5 minutes to about 100 minutes, or about 10 minutes to about 90 minutes. In certain examples, the treatment step is carried out for a period of time of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 155, 160, 165, 170, 175, 180, 185, 190, 195, 200, 205, 210, 215, 220, 225, 230, 235, 240 minutes, or any range therein. In particularly preferred examples, the treatment step is carried out for a period of time of about 15 minutes to about 120 minutes.

For the treatment step, the agent is suitably present at an amount of about 10% to about 200% or any range therein, such as, but not limited to, about 20% to about 150%, about 30% to about 100%, or about 50% to about 70% by weight of the resinous wood (i.e., the agent to resinous wood ratio). In particular embodiments, the agent is present at about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, 200% or any range therein, by weight of the resinous wood.

Suitably, the resinous wood is treated with an agent that comprises, consists or consists essentially of a terpene. In this regard, the agent may be considered a terpene based solvent. A terpene, including those described herein and mixtures thereof, can be present in the agent in an amount from about 50% to about 100% by weight of the agent or any range therein, such as, but not limited to, about 60% to about 80%, about 70% to about 90%, or about 80% to about 100% by weight of the agent. In particular examples of the present disclosure, a terpene is present in the agent in an amount of about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% or any range therein, by weight of the agent. In particularly preferred examples of the present disclosure, the terpene is present in an amount from about 90% to about 100% by weight of the agent.

In a further embodiment, the terpene of the agent has, at least in part, been recovered, recycled or derived from a terpene fraction previously extracted from the resinous wood and/or the agent previously used to treat the resinous wood. In this regard, the recovered, recycled or derived terpene may be in a partially or fully purified or refined form. In this regard, the present method may include the further step of recycling the terpene fraction extracted from the resinous wood and/or the agent for use in or as the agent in the treatment step. Accordingly, the agent can comprise the same or similar composition of terpenes as the terpene fraction to be extracted thereby. Additionally, the recovered or recycled terpene described herein, may be subjected to one or more processes, such as purification or filtration, to render it more suitable and/or advantageous for use in the present disclosure without converting it to "pure" or technical grade/refined (e.g., >97% purity) terpene or turpentine.

Suitably, the method of the present disclosure at least partially extracts the rosin and/or terpene fractions present in the resinous wood. To this end, the present method may extract 100% or less than 100% of the rosin and/or terpene fractions present in the resinous wood. In particular examples, the present method may result in the extraction and/or recovery of about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100% or any range therein, of the rosin and/or terpene fractions present in the resinous wood compared or relative to the amount of the rosin and/or terpene fractions present in the resinous wood before treatment with the method described herein.

Suitably, the resinous wood is in a subdivided or fragmented form for treatment by the method described herein. To this end, the resinous would can include chips, flakes, strands, pellets or the like. As such, the method of the present aspect further includes the earlier or preceding step of desizing, subdividing, fragmenting or reducing the resinous wood (e.g., chipping, grinding, flaking, shredding, pulverising) prior to treatment with the agent, but after harvesting of the resinous wood. In this regard, solid wood, such as logs and stumps, is suitably subdivided into smaller pieces or fragments, such as strands, fibers, flakes and/or chips, prior to treatment thereof so as to aid extraction of the rosin and/or terpene fractions therefrom. In some examples, the resinous wood is subjected to a desizing step to achieve a target particle size, such as that described herein Accordingly, the resinous wood suitably comprises wood chips or flakes derived from one or a plurality of resinous trees, such as those hereinbefore described. It is further envisaged that the wood can be subdivided by any suitable means known in the art, with a conventional wood chipper and/or a hammer mill being preferred.

In view of the above, the resinous wood can include wood portions having a volume of between about 0.01 $cm^3$ and about 1 $cm^3$ (e.g., about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1 $cm^3$ or any range therein).

Furthermore, the resinous wood to be treated by the agent can include wood portions having a surface area of between about 0.03 $cm^2$ and about 0.5 $cm^2$ (e.g., about 0.03, 0.04, 0.05, 0.06, 0.07, 0.08, 0.09, 0.1, 0.15, 0.2, 0.25, 0.3, 0.35, 0.4, 0.45, 0.5 $cm^2$ or any range therein).

Moreover, the resinous wood can include wood portions having a dimension, such as a length, width or diameter, of between about 0.01 cm and about 1 cm (e.g., about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1 cm or any range therein). In some examples, the dimension of the wood portions is between about 0.1 to about 0.35 cm.

Based on the above, the method of the present aspect may further include the step of screening the resinous wood prior to treatment with the agent so as to ensure an appropriate size and/or surface area thereof. Portions of the resinous wood that are removed or selected out by this screening step may then be subjected to a further subdividing step until an appropriate size or surface area is achieved for treatment with the agent. Accordingly, the resinous wood can be screened prior to treatment to remove wood portions having a volume, surface area and/or dimension greater than any of those aforementioned values. In some examples, the resinous wood is screened prior to treatment to remove wood portions having a dimension, such as a length, width or diameter, greater than about 0.15 cm, greater than about 0.20 cm, greater than about 0.25 cm, greater than about 0.30 cm, greater than about 0.35 cm, greater than about 0.40 cm, greater than about 0.45 cm or greater than about 0.50 cm.

Generally, the period of time between the initial step of subdividing the resinous wood and treating the resinous wood with the agent may be no more than about 12 hours (e.g., 12, 11, 10, 9, 8, 7, 6, 5, 4, 3, 2, 1, 0.5, 0.25, 0.1 hours or any range therein), no more than about 8 hours, no more than about 4 hours, no more than about 2 hours, no more than about 1 hour, no more than about 30 minutes, no more than about 15 minutes or no more than about 5 minutes. In this regard, the skilled person will appreciate that the step of treating the resinous wood may occur almost immediately after the present subdividing step. Again, this ensures that the terpene and rosin fractions are retained within the log or wooden core as long as possible without loss of the terpene portion due to evaporation and/or adversely affecting rosin fraction quality due to oxidation.

Suitably, the method of the present aspect further includes the step of separating the rosin fraction from the terpene fraction extracted from the resinous wood. As used herein, the term "separating the rosin fraction from the terpene fraction" means separating a mixture of molecules containing rosin and terpenes, into a first fraction of molecules with a higher concentration of or substantially containing rosin and a second fraction of molecules containing a higher concentration of or substantially containing terpenes, including terpenes from the agent. In this regard, it will be appreciated that the terpene fraction may be separated from the rosin fraction together with the agent, as the agent also comprises terpenes and is preferably derived from a terpene fraction previously extracted from resinous wood, as described herein. It is envisaged that such separating may be performed by any method or means known in the art, such as distillation, fractionation, chromatographic separation, crystallisation, extraction and the like.

In some examples, the respective rosin and terpene fractions are separated, at least partly, by distillation. The term "distillation" refers to the process of physically separating chemical components into a vapour phase or stream and a liquid phase or stream based on differences in the respective components' boiling points and vapour pressures at specified temperatures and pressures. Distillation is typically performed in a distillation column or chamber, which usually includes a series of vertically spaced plates. A feed stream enters the distillation column at a mid-point, dividing the distillation column into two sections. The top section may be referred to as the rectification section, and the bottom section may be referred to as the stripping section. Condensation and vaporization occur on each plate, causing lower boiling point components, such as the terpene fraction, to rise to the top of the distillation column and higher boiling point components, such as the rosin fraction, to fall to the bottom. A re-boiler is located at the base of the distillation column to add thermal energy. As those skilled in the art will appreciate, recovery of energy and recycling of process streams can be applied to improve plant efficiencies. The "bottoms" product or liquid stream, which for the present disclosure comprises, consists of or consists essentially of the rosin fraction, can then be directly removed from the base of the distillation column. A reflux pump is generally used to maintain flow in the rectification section of the distillation column by pumping a portion of the distillate back into the distillation column.

A condenser is typically located at the top of the distillation column and operably connected thereto to condense the vapour or gaseous stream emanating from the top of the distillation column and produce a distillate. The associated condenser and liquid separation vessels that may be employed with the distillation columns may be of any conventional design. For the present disclosure, the distillate suitably comprises the terpene fraction and the agent used to extract the terpene fraction and optionally a water fraction if steam is used in the distillation process. As such, the present method may further include the step of separating the terpene fraction and/or the agent from the distillate, particularly if the distillate comprises, for example, a water fraction.

Suitably, the distillation conditions, such as feed rates, feed pressures, feed temperatures, column pressures, column temperatures, reflux rates, distillation times etc are appropriate for efficient separation of the rosin and terpene fractions (inclusive of the agent) in the distillation column.

In particular examples, during the distillation step the mixture of the terpene fraction, the rosin fraction and the agent is heated to between about 150° C. and about 250° C.

As will be appreciated by the skilled person, one or more steps, or part thereof, of the method of this aspect may also be performed under pressure or vacuum. By way of example, one or more steps of the method, or part thereof, of the present disclosure are performed at a pressure of about 0 psi to about 120 psi or any range therein such as, but not limited to, about 25 psi to about 75 psi, or about 40 psi to about 60 psi. In particular examples of the present disclosure, one or more steps of the method, or part thereof, are performed at a pressure of about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 psi or any range therein. In some examples, the step of treating the resinous wood with the agent, or part thereof, is performed at a pressure of about 10 psi to about 75 psi. In various examples, the step of separating the terpene fraction and the rosin fraction, or part thereof, is performed at a pressure of about 25 psi to about 120 psi.

Suitably, the method of the present aspect further includes the subsequent step of heating or heat treating the resinous wood treated with the agent to at least partly remove residual portions of the agent and/or the terpene fraction therefrom. It is envisaged that such heating may be performed by any method or means known in the art to thermally evaporate residual portions of the agent and the terpene fraction from the treated resinous wood. In particular examples, the treated resinous wood is heat treated at a temperature of about 150° C. to about 300° C. (e.g., about 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300° C. or any range therein). This heat treatment step may also be performed for a period of time from about 5 minutes to about 30 minutes (e.g., about 5, 10, 15, 20, 25, 30 minutes or any range therein).

In particular examples, the resinous wood is steam treated after being treated with the agent, such as in a desolventiser or desolventiser-toaster, to produce a further gaseous stream. This further gaseous stream may be contacted with a further separator, such as a further condenser or the like so as to facilitate separation of a further portion of the agent and the terpene fraction from a water fraction derived from the steam. Given the difference in densities between the agent/terpene fraction and the water fraction, gravity separation can be used for separation with the less dense agent/terpene fraction floating on top of the denser water fraction. The residual portions of the agent and terpene fractions can then be removed from the further separator or condenser and transferred to a central storage vessel as required.

It will be appreciated that the resinous wood may have downstream uses following treatment by the method described herein. By way of example, the treated resinous wood may be utilised as a mulch, animal bedding (due to being sterilised in process), a cleaned or concentrated source of lignin and/or cellulose for further chemical production and a feedstock for wood pellets or biofuels, without limitation thereto. In some examples, the treated resinous wood is further treated, such as by methods known in the art (e.g., Kraft pulping; see also PCT/AU2015/050389), to produce a cellulosic material suitable for paper, cardboard and textile production. In other examples, the treated resinous wood is further treated, such as by methods known in the art (see, e.g., PCT/AU2015/050390), to produce a partially hydrolysed lignocellulosic material that is suitable for downstream fermentable sugar and biofuel production.

In some examples, the method further comprises a final scrubbing step of a residual gaseous stream. In this regard, a residual gaseous stream from one or more of the separators or condensers may be contacted with a scrubbing device, such as a wet scrubber or other scrubbing device known in the art, to remove any further residual terpene fraction and/or agent therefrom. This further residual terpene fraction and/or agent may then be separated by yet another separator or condenser or decanting and transferred to a central storage vessel for the terpene fraction and the agent.

Suitably, the rosin and/or terpene fractions extracted from the resinous wood by the method of the present aspect are free or substantially free of contaminants (e.g., has no more than about 0.5%, 0.2%, 0.1% or 0.05% contaminants by weight of the fraction), such as may be present for other solvent or tapping extraction methods known in the art (e.g., hexanes, methyl ethyl ketone, hydrocarbons, petrochemicals, sulphides, sulphates, heavy metals, acids, growth hormones etc)

In some examples, the terpene fraction comprises about 50% to about 100% pinenes (e.g., about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% or any range therein) by weight of the fraction. As used herein, the term "pinene" refers to a bicyclic monoterpene chemical compound of formula (1S,5S)-2,6,6-trimethylbicyclo[3.1.1]hept-2-ene. There are two structural isomers of pinene found in nature: α-pinene and β-pinene, both of which are chiral. Pinene as used herein may be α-pinene, pinene, or a mixture thereof, such as a 50-50 mixture. As will be appreciated by the skilled person, the component and/or percentage pinenes of the terpene fraction may vary with, for example, the type, species and age of the resinous wood.

The terpene fraction extracted from the resinous wood suitably comprises less than about 25% (e.g., less than about 25%, 24%, 23%, 22%, 21%, 20%, 19%, 18%, 17%, 16%, 15%, 14%, 13%, 12%, 11%, 10%, 9%, 8%, 7%, 6%, 5%, 4.5%, 4%, 3.5%, 3%, 2.5%, 2%, 1.5%, 1%, 0.5%, 0.4%, 0.3%, 0.2%, 0.1% or any range therein) of a terpene polymer, such as diterpenes and triterpenes, by weight thereof. In this regard, the terpene fraction may be considered to be free or substantially free of terpene polymers. The term "terpene polymer" is used herein to refer to an oligomer or a polymer containing one or more structural repeating units derived from a terpene. These may comprise, for example, homopolymers and copolymers.

The terpene fraction extracted from the resinous wood suitably comprises less than about 15% (e.g., less than about 15%, 14%, 13%, 12%, 11%, 10%, 9%, 8%, 7%, 6%, 5%, 4.5%, 4%, 3.5%, 3%, 2.5%, 2%, 1.5%, 1%, 0.5%, 0.4%, 0.3%, 0.2%, 0.1% or any range therein) of a synthetic pine oil, such as terpene alcohols, by weight thereof. In this regard, the terpene fraction may be considered to be free or substantially free of synthetic pine oils. To this end, the absence of an acid from the present extraction method advantageously prevents or minimises the conversion of α- and β-pinenes to synthetic pine oils.

Suitably, the rosin fraction extracted from the resinous wood is near colourless or very light in colour. In certain examples, the rosin fraction has a Gardner colour number of no more than about 8 (e.g., about 8, 7.5, 7, 6.5, 6, 5.5, 5, 4.5, 4, 3.5, 3, 2.5, 2, 1.5, 1 and any range therein). In particular examples, the rosin fraction has a Gardner colour number of no more than about 5. In other examples, the rosin fraction has a Gardner colour number of no more than about 3. In this regard, the present method advantageously facilitates the production of a rosin fraction having little or no colour, which is a known drawback of prior art solvent extraction methods (see, e.g., U.S. Pat. No. 4,906,733).

As used herein, the term "Gardner colour" refers to a visual scale and was originally developed to describe the colour of commercially available chemical products, such as rosin. The lower the value of the Gardner scale, the lighter the colour of the chemical product. Colouration of the rosin fraction can be determined by any means known in the art, such as by comparison with a Lovibond disc. The skilled person would further appreciate that colour charts that define colour, such as those that define rosin colour from M, N, WG, WW, X and XA, may also be used to estimate colour of the rosin fraction or as a substitute of the Gardner scale (e.g., X or WW being 5 on the Gardner scale). In particular examples, the rosin fraction described herein has not been subjected to any further decolourisation step/s (e.g., contacted with a decolourisation agent), as is known in the art (see, e.g., U.S. Pat. No. 4,906,733).

In particular examples, the rosin fraction has an acid value between about 160 to about 175 (e.g., about 160, 161, 162, 163, 164, 165, 166, 167, 168, 169, 170, 171, 172, 173, 174, 175 and any range therein). In certain examples, the rosin fraction has an acid value between about 162 to about 170. In one examples, the rosin fraction has an acid value of about 165. The skilled artisan will understand that the acid value is the mass of potassium hydroxide (KOH) in milligrams that is required to neutralize one gram of a chemical substance or in this case rosin or a rosin derivative. To this end, the acid value is a measure of the amount of carboxylic acid groups present in the rosin fraction. Determining the acid value of the rosin fraction can be performed by any method known in the art, such as by titration with KOH of a solution of rosin in a suitable solvent using an indicator to determine the endpoint (e.g., as described in ASTM method D 465-05 (2010)).

Suitably, the rosin fraction comprises an abietic acid content or concentration in the range from about 15% to about 35% (e.g., about 15, 16, 17, 18, 19, 20, 21, 22, 23, 24, 25, 26, 27, 28, 29, 30, 31, 32, 33, 34, 35% or any range therein) by weight of the rosin fraction. In some specific examples, the abietic acid content of the rosin fraction is about 15% to about 25% or about 15% to about 20% by weight thereof. In one particular example, the abietic acid content of the rosin fraction is about 20%. The skilled artisan will appreciate that abietic acid is a primary component of rosin and is an abietane diterpenoid that is abieta-7,13-diene substituted by a carboxy group at position 18.

In a further aspect, the disclosure provides a terpene fraction produced according to the method hereinbefore described.

As such, the terpene fraction can be that hereinbefore described.

In some examples, the terpene fraction comprises at least about 65%, at least about 70%, at least about 75% or at least about 80% pinenes (e.g., about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% or any range therein) by weight of the terpene fraction.

In various examples, wherein the terpene fraction is substantially free of contaminants.

In particular examples, the terpene fraction comprises less than about 20%, less than about 10%, less than about 5%, less than about 2.5% or less than about 1% terpene polymers, such as diterpenes and triterpenes, by weight of the terpene fraction.

In certain examples, the terpene fraction comprises less than about 15%, less than about 10%, less than about 5%, less than about 2.5%, less than about 1% or less than about 0.5% of a synthetic pine oil by weight thereof.

In a related aspect, the disclosure provides an isolated terpene fraction that comprises one or more of the below features:

(a) at least about 65%, at least about 70%, at least about 75% or at least about 80% pinenes by weight of the isolated terpene fraction;
(b) substantially free of contaminants;
(c) less than about 25%, less than about 10%, less than about 5%, less than about 2.5% or less than about 1% terpene polymers by weight of the isolated terpene fraction; and
(d) less than about 15%, less than about 10%, less than about 5%, less than about 2.5%, less than about 1% or less than about 0.5% synthetic pine oil by weight of the isolated terpene fraction.

In a particular example, the isolated terpene fraction is or comprises: at least about 75% pinenes by weight thereof, substantially free of contaminants; comprises less than about 2.5% terpene polymers by weight thereof; and less than about 2.5% synthetic pine oil by weight thereof.

For the purposes of the present disclosure, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Suitably, the isolated material is in a native or near-native form.

In another aspect, the disclosure resides in a rosin fraction produced according to the method of the first mentioned aspect.

As such, the rosin fraction can be that hereinbefore described.

In certain examples, the rosin fraction has a Gardner colour number of no more than about 8.

In various examples, the rosin fraction is substantially free of contaminants.

In particular examples, the rosin fraction has an acid value between about 160 to about 175.

In another related aspect, the disclosure provides an isolated rosin fraction that comprises one or more of the below features:

(a) a Gardner colour number of no more than about 8, no more than about 5 or no more than about 3;
(b) free or substantially free of contaminants;
(c) an acid value between about 160 to about 175 (e.g., about 160, 161, 162, 163, 164, 165, 166, 167, 168, 169, 170, 171, 172, 173, 174, 175 and any range therein); and
(d) an abietic acid content in the range from about 15% to about 35% (e.g., about 15%, 16%, 17%, 18%, 19%, 20%, 21%, 22%, 23%, 24%, 25%, 26%, 27%, 28%, 29%, 30%, 31%, 32%, 33%, 34%, 35% and any range therein), about 15% to about 25% or about 15% to about 20% by weight of the isolated rosin fraction.

In particular examples, the isolated rosin fraction is or comprises: a Gardner colour number in the range of about 3 to about 5; free or substantially free of contaminants; an acid value between about 163 to about 170; and an abietic acid content in the range from about 17% to about 22%.

In certain examples, the isolated rosin fraction is or comprises: a Gardner colour number of about 3; free or substantially free of contaminants; an acid value between of about 165; and an abietic acid content of about 20%.

In another aspect, the disclosure provides a method of making a polymer, said method including the step of treating, such as chemically treating, a rosin fraction and/or a terpene fraction produced according to the method described herein to thereby make the polymer. In some examples, the method is directed to making a rosin polymer, said method including the step of treating a rosin fraction produced according to the method described herein to thereby make the rosin polymer. In other examples, the method is directed to making a terpene polymer, said method including the step of treating a terpene fraction produced according to the method described herein to thereby make the terpene polymer.

In a related aspect, the disclosure relates to a polymer produced according to the aforementioned aspect.

The term "polymer" refers to a compound prepared by polymerizing monomer units, such as terpene and rosin monomer units, whether of the same or a different type. The generic term polymer thus embraces the term homopolymer (i.e., polymers prepared from only one type of monomer), and the term "interpolymer" (i.e., polymers prepared by the polymerization of at least two different types of monomers).

Polymerized rosin compounds typically have a high level of pigment dispersing ability, compatibility, cohesion and adhesion, and other properties, and therefore are advantageously used as binders or additives in a wide variety of fields such as printing ink, paint, pressure-sensitive adhesives or adhesives, and flux. Terpene polymers may also be utilised as bioplastics and biofuels.

A variety of methods have been utilised for producing polymerized rosin compounds and polymerized terpene compounds. These may include, for example, using a solvent (e.g., an organic solvent, such as toluene or xylene) and/or a catalyst, such as an acid catalyst (e.g., aliphatic sulfonic acid, formic acid, p-toluenesulfonic acid, methanesulfonic acid), a metal catalyst and a Friedel-Crafts catalyst.

In another aspect, the disclosure provides a method of making an ester, said method including the step of treating a rosin fraction and/or a terpene fraction produced according to the method described herein to thereby make the ester. The method may include esterifying the rosin fraction and/or the terpene fraction with an esterification agent, such as an alcohol.

In some examples, the method is directed to making a rosin ester, said method including the step of treating a rosin fraction produced according to the method described herein to thereby make the rosin ester.

In other examples, the method is directed to making a terpene ester, said method including the step of treating a terpene fraction produced according to the method described herein to thereby make the terpene ester.

The term "ester" broadly defines a chemical compound derived from an acid (e.g., organic or inorganic) in which at least one —OH (i.e., hydroxyl) group is replaced by an —O-alkyl (i.e., alkoxy) group.

The carboxylic acid group of a rosin fraction can be converted to a rosin ester through a reaction with one or more alcohols, such as glycerol, pentaerythritol, methanol and tri-ethylene-glycol. In some examples, the ester or rosin ester is or comprises a glycerol ester of rosin. By way of example, the rosin fraction can be reacted or treated with glycerine, such as food grade glycerine, to produce the glycerol ester. Glycerol esters of rosin represent an oil-soluble food additive also known as glyceryl abeitate or ester gum. Glycerol ester of rosin acts as a stabilizer and/or a thickening agent some foods and beverages. It is a food-grade material used in foods, beverages, and cosmetics to keep oils in suspension in water. Exemplary foods and beverages that contain glycerol ester of rosin include fruit and citrus flavoured sodas, lemonades, vitamin-enhanced waters, sports drinks, chewing gum, fruit coatings and confectionary inks.

In a related aspect, the disclosure relates to an ester produced according to the method of the previous aspect.

In a final aspect, the disclosure provides an apparatus or system for extracting rosin and/or terpene fractions from a resinous wood comprising: a treatment chamber for treating the resinous wood with an agent that comprises, consists or consists essentially of a terpene.

In some examples, the treatment chamber is or comprises a counter-current extractor, such as those hereinbefore described.

In certain examples, the apparatus further comprises a distillation chamber in communication with the treatment chamber, the distillation chamber for separating the rosin and terpene fractions extracted from the resinous wood.

In various examples, the apparatus further comprises a desolventiser in communication with the treatment chamber, the desolventiser capable of heating, such as steam treating, the resinous wood treated with the agent so as to at least partly remove residual portions of the agent and/or the terpene fraction therefrom.

In particular examples, the apparatus further comprises a separator, such as a condenser, in communication with the distillation chamber, the separator for separating the terpene fraction from a distillate produced by the distillation chamber.

In some examples, the apparatus further comprises a scrubbing device, such as a wet scrubber.

In some examples, the apparatus is configured for operating in a continuous or semi-continuous manner.

Suitably, the apparatus is for use in the method of the first aspect.

A particular embodiment of the apparatus or system 10 is shown in FIG. 1. In referring to FIG. 1, the apparatus 10 comprises a first shredder 15 for subdividing the resinous wood prior to entry into a treatment chamber 20. Once the resinous wood is subdivided by the first shredder it is transferred to a screen 16 for filtering out any over-sized and/or under-sized portions of the resinous wood. These over-sized portions may then be transferred to a second shredder (not shown) or back to the first shredder 15 to reduce them to a suitable size for treatment.

Following the screening process, appropriately sized portions of the resinous wood are transferred to a storage bin 17 in communication with the treatment chamber 20. The storage bin 17 functions to level out the resinous wood stored therein and control the amount of the resinous wood entering the treatment chamber 20, with the treatment chamber 20 comprising an inlet for receiving the resinous wood to be treated with an agent comprising a terpene, as described previously.

The treatment chamber 20 is designed to treat the resinous wood with the agent in a counter-flow manner under user specified temperatures and/or pressures, such as those hereinbefore provided. Suitably, there is little or no agitation of the resinous wood whilst in the treatment chamber 20. In the embodiment provided, the treatment chamber 20 is or comprises a rotary extractor, such as a rotocel extractor, which generally comprises a cylindrical chamber that contains a plurality of separated treatment cells (not shown) for receiving the resinous wood therein. The cylindrical chamber 21 rotates around a central shaft at a desired rate, whilst the agent is applied as a spray to the separated treatment cells. In this regard, the treatment chamber 20 may include a number of nozzles or spray applicators (not shown) for spraying the agent onto the resinous wood.

As it moves through the treatment chamber 20, the resinous wood is progressively treated whilst in the treatment cell by way of the spray applicators. Spray applicators deliver the agent onto the resinous wood, after which the agent, the terpene fraction and/or rosin fraction drains therefrom and collects by gravity or vacuum into respective collection trays. “Fresh” agent (i.e., agent which contains no or only a low concentration of the rosin fraction) is provided by a spray applicator at or towards the end of the treatment cycle whereafter it enters at a final or distal collection tray and flows counter to the movement of the resinous wood through the treatment chamber 20.

In this regard, the agent that has collected in the collection trays is then pumped back through pipes or conduits to their respective sprayers. In this manner, the treatment chamber 20, allows for continuous or semi-continuous counter-current treatment or contacting of the resinous wood with the agent to partially or completely remove the rosin and terpene fractions therefrom with minimal agent use. The agent that has collected in the most proximal collection tray typically contains the highest concentration of the terpene and rosin fractions extracted from the resinous wood and it is subsequently transferred by a pipe to a distillation column 25. Thus, the cleanest or freshest agent contacts the “cleanest” resinous wood, and the agent with the highest concentration of rosin contacts the resinous wood immediately as it enters the treatment chamber 20.

It will also be appreciated that in alternative examples, the rotary extractor may be replaced by conveyors, such as belt conveyors, that facilitate movement of resinous wood through the treatment chamber 20.

As can be seen from FIG. 1, the apparatus 10 further includes a distillation column in fluid or gaseous communication with the treatment chamber 20, the distillation column configured to promote separation of the terpene fraction and the agent from the rosin fraction. For the present embodiment, the distillation column 25 is a continuous steam distillation column and steam distillation may be carried out by a conventional steam distillation method, as are known in the art. The distillation chamber 25 comprises a series of vertically spaced plates 26, a re-boiler 27 positioned at a base thereof and a first condenser 30 connected to a top portion thereof and in fluid communication therewith. A feed stream from the treatment chamber 20 which contains the agent, the terpene fraction and the rosin fraction enters the distillation column 25 at or towards a mid-point thereof via an inlet (not shown) and contacts the plates, which results in the production of a gaseous stream containing the agent, the terpene fraction and a water fraction from the added steam and a liquid stream containing the rosin fraction. The liquid stream containing the rosin fraction collects at the base of the distillation column 25 and can then be directly removed from the distillation column 25 for storage in a storage vessel 35.

The gaseous stream rises within the distillation chamber 25 and collects in the first condenser 30, which cools the component terpene fraction, the agent and water fraction into a distillate. Based on their respective densities, the terpene fraction and the agent separate from the water fraction by gravity and can then be decanted off and transferred to a central storage chamber 40.

Referring to FIG. 1, the apparatus 10 further comprises a desolventiser 50 to which the resinous wood may be transferred following treatment with the agent. The desolventiser 50 is designed to heat treat the treated resinous wood with superheated steam. The desolventiser 50 comprises a chamber having a floor, and above the floor are positioned a series of permeable trays for receiving the resinous wood thereon. The trays are heated by and allow passage of the steam (and/or other heating medium such as oil) therethrough for heating and permeating the resinous wood. Accordingly, a further gaseous stream containing a mixture of the steam and vaporized residual portions of the agent and the terpene fraction flows upwardly in the desolventiser 50 to a second condenser 60 operably connected thereto. Similar to the first condenser 30, the second condenser 60 is designed to separate the residual portions of the agent and the terpene fraction from a water fraction derived from the superheated steam. Once separated, the residual portions of the agent and the terpene fraction can be transferred to the central storage chamber 40.

As shown in FIG. 1, the apparatus further comprises a wet scrubber 70. The skilled person will appreciate that the wet scrubber 70 is designed to protect the apparatus or system 10 from high pressures or over-pressurising with each condenser 30,60 having a waste gas or volatile gas vent (not shown) that is sealed and connected by a pipe to the wet scrubber 70. The wet scrubber 70 functions by spraying water onto a gaseous stream derived from the first and second condensers 30,60 and bubbling the gaseous stream through a level of oil to further capture any uncondensed gases, such as terpene containing gases. This process can be controlled by a suitably situated vacuum pump 80 that generates a slight vacuum to ensure good vapour or gaseous flow through the condensers 30,60 and finally to atmosphere for any incondensable gases. Any terpene fraction extracted by the wet scrubber 70 may further be transferred to the central storage chamber 40.

Particular aspects of the present disclosure are described in the following numbered Statements, which illustrate the exemplary application of the present disclosure to coniferous wood. It will be understood that the present disclosure is not limited to these exemplary applications to coniferous wood.

1. A method for extracting rosin and/or terpene fractions including components or derivatives thereof from a coniferous wood, said method including the step of treating/contacting the coniferous wood with an agent that comprises, consists or consists essentially of a terpene to thereby extract the rosin and/or terpene fractions from the coniferous wood.

2. The method of Statement 1, further including the initial step of subdividing the coniferous wood.

3. The method of Statement 2, wherein the period of time between the initial step of subdividing the coniferous wood and treating the coniferous wood with the agent is no more than about 8 weeks, no more than about 4 weeks or no more than about 2 weeks.

4. The method of any one of the preceding Statements, further including the step of separating the rosin fraction and the terpene fraction extracted from the coniferous wood.

5. The method of Statement 4, wherein separating the rosin fraction and the terpene fraction is performed at least in part by distillation to produce a distillate that comprises, consists essentially of or consists of the terpene fraction and a residual stream that comprises, consists essentially of or consists of the rosin fraction.

6. The method of Statement 5, further including the step of separating the terpene fraction from the distillate.

7. The method of any one of the preceding Statements, further including the subsequent step of heating the coniferous wood treated with the agent to at least partly remove residual portions of the agent and/or the terpene fraction therefrom.

8. The method of any one of the preceding Statements, wherein the step of treating the coniferous wood with the agent is performed for a period of time from about 15 minutes to about 120 minutes.

9. The method of any one of the preceding Statements, wherein the step of treating the coniferous wood with the agent is performed at a temperature from about 75° C. to about 135 oc.

10. The method of any one of the preceding Statements, wherein the step of treating the coniferous wood with the agent is performed at a pressure of about 10 psi to about 75 psi.

11. The method of any one of the preceding Statements, wherein the coniferous wood is treated in a counter-current/counter-flow manner with the agent.

12. The method of any one of the preceding Statements, wherein the rosin and/or terpenes fractions extracted from the coniferous wood are substantially free of contaminants.

13. A terpene fraction produced according to the method of any one of Statements 1 to 12.

14. The terpene fraction of Statement 13, comprising at least about 65%, at least about 70%, at least about 75% or at least about 80% pinenes.

15. The terpene fraction of Statement 13 or Statement 14, wherein the terpene fraction is substantially free of contaminants.

16. The terpene fraction of any one of Statements 13 to 15, comprising less than about 20%, less than about 10%, less than about 5%, less than about 2.5% or less than about 1% terpene polymers, such as diterpenes and triterpenes.

17. A rosin fraction produced according to the method of any one of Statements 1 to 12.

18. The rosin fraction of Statement 17, having a Gardner colour number of no more than about 8.

19. The rosin fraction of Statement 17 or Statement 18, wherein the rosin fraction is substantially free of contaminants.

20. The rosin fraction of any one of Statements 17 to 19, having an acid value between about 160 to about 175.

21. An apparatus for extracting rosin and/or terpene fractions from a coniferous wood comprising: a treatment chamber for treating the coniferous wood with an agent that comprises, consists or consists essentially of a terpene.

22. The apparatus of Statement 21, wherein the treatment chamber is or comprises a counter-current extractor.

23. The apparatus of Statement 21 or Statement 22, further comprising a distillation chamber in communication with the treatment chamber, the distillation chamber for separating the rosin and terpene fractions extracted from the coniferous wood.

24. The apparatus of any one of Statements 21 to 23, further comprising a desolventiser in communication with the treatment chamber, the desolventiser for heating the coniferous wood treated with the agent so as to at least partly remove residual portions of the agent and/or the terpene fraction therefrom.

25. The apparatus of any one of Statements 21 to 24, further comprising a separator in communication with the distillation chamber, the separator for at least partly separating the terpene fraction from a distillate produced by the distillation chamber.

25. The apparatus of any one of Statements 21 to 25, further comprising a scrubbing device.

26. The apparatus of any one of Statements 21 to 25, for use in the method according to any one of Statements 1 to 12.

In order that the invention may be readily understood and put into practical effect, particular preferred embodiments will now be described by way of the following non-limiting examples.

Example 1

This Example relates to desizing and size distribution of the resinous wood to be treated by the method described herein.

Wood Processing

Several tonnes of resinous pine stumps and logs are passed through a Vermeer Grinder at fast in feed settings to create a large chip to be subsequently fed into hammer mill. The chip is loaded into a bin feed hopper to modulate flow into the treatment process. The bin feed flows onto conveyors to direct flow of the woodchip to the hammer mill.

In this Example, the aim was to reduce chip size to a dimension of ⅛ inch-½ inch (3.175 mm-12.7 mm) with minimal deviation from this range. Chips finer than 3 mm can pass through the sieves and go forward into the extractor without issue.

Figure 2:
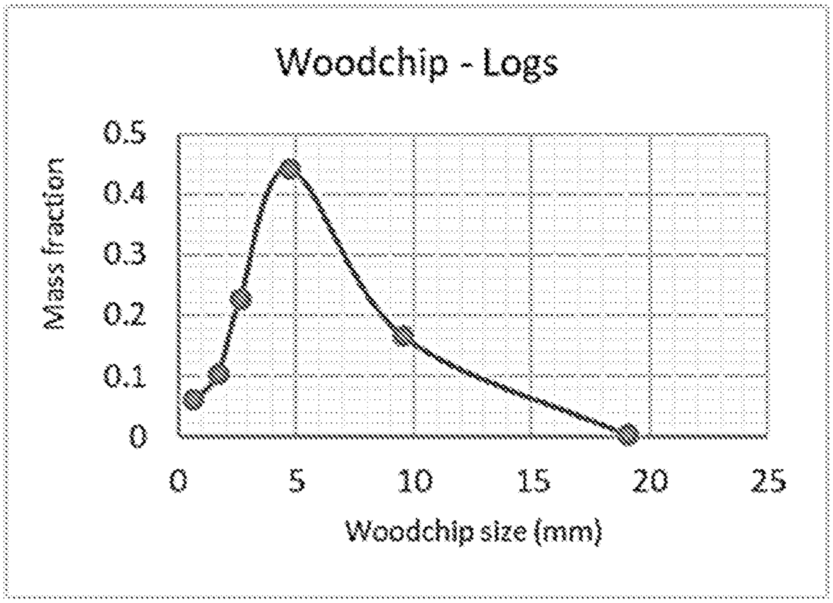
FIG. 2 demonstrates the woodchip size distribution for logs (A) and stumps (B).
Figure 2:
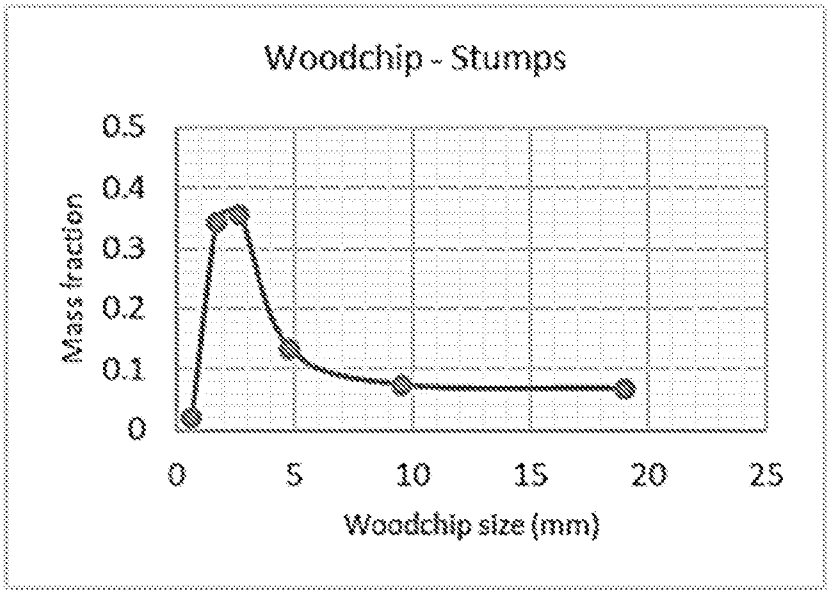

Size distribution of the woodchip data is shown in FIGS. 2A-B. As shown in these figures, the majority of the de-sized resinous wood is of a suitable size for subsequent treatment in the extractor or treatment chamber.

TABLE 1

| Woodchip characteristics | |
|---|---|
| Log woodchip: | Stump woodchip: |
| Mean size: 4.55 mm (0.18 inch)<br>Standard deviation: 2.69 mm (0.11 inch)<br>Bulk density: 312.65 kg/m$^3$<br>Woodchip <3.175 mm: 39% | Mean size: 4.2 mm (0.17 inch)<br>Standard deviation: 4.53 mm (0.18 inch)<br>Bulk density: 266.90 kg<br>Woodchip <3.175 mm: 72% |

Bulk Density

Bulk density of woodchip from logs passed through chipper and hammer mill: 312.65 kg/m$^3$ Bulk density of woodchip from stumps passed through Vermeer grinder and hammer mill: 266.9 kg/m$^3$

Example 2

This Example provides an embodiment of plant operating conditions for terpene and rosin extraction based on the methods described herein.

Feed Rate

Given the volume of the treatment chamber or extractor and current bulk density of the wood chip to be treated, the present system is compatible with about 125 as is tonnes per day for stumps or 150 tonnes per day for logs.

Extractor Conditions/Solvent Feed

- Full rotation of woodchip is 1.5 hr—retention time in extractor
  - Washing time with extraction agent: between about 45 minutes to about 60 minutes (e.g., ~53 minutes)
  - Solvent to wood ratio (i.e., solids to liquids ratio) in extractor is about 0.50 to 0.60 (range of about 0.3 to about 1.5 depending on flow of woodchip and solvent).
  - 6 solvent sprayers are spaced around just over the first half of the rotation to apply extraction agent to the woodchip
  - Remainder of time (~40-50 minutes) in extractor is to drain woodchip before the exit chute, and exit time.
- Temperature of solvent/agent washing woodchip is about 90-100° C. Heaters are present on each of the recirculation lines to maintain the temperature in extractor.
- Solvent/agent feed rate to extractor at 50 L/min at 90° C.

Desolventiser

Solvent/agent treated woodchip from the extractor is then fed into the desolventiser. The solvent/agent treated woodchip is approximately 25% solvent saturated (dry woodchip weight+25% terpenes). The time taken for woodchip to travel from stages 1-5=1 min 30 seconds with a final retention time in 5$^{th}$ stage with live steam injection=~9 minutes.

Distillation Chamber

The respective rosin and terpene fractions may be separated from each other in the distillation chamber as hereinbefore described.

Results

Terpenes:

- Current observed yield: Average=~1.1% for logs and ~4.3% for stumps; Range=1-5% (dependent on the composition of the initial feedstock of resinous wood)
- Colour: straw to pale yellow Rosin:

- Colour of rosin produced: translucent reddish-brown
- Acid number: Observed Range=160-175
- Dropping point: Observed Range=69 to 75° C.
- Yield: Average=~8%; Range ~5-20% (dependent on the composition of the initial feedstock of resinous wood)

Tables 2 and 3 provide an example of the physicochemical properties of the rosin and terpene fractions extracted by the method described herein.

TABLE 2

Characteristics of extracted rosin

| Characteristic | Value |
|---|---|
| Acid Index | 164.91 |
| Melting point ° C. | 69 |
| Gardner Colour | 3(+) |
| Colour USDA | X |
| Sulphides | Negative |
| Infrared | Normal |
| Viscosity (Brookfield 100° C.) | 2895 cps |
| Abietic acid % | 19.94 |
| Dehydroabietic acid % | 6.44 |
| Palustric acid % | 25.22 |
| Sandaracopimaric acid % | 4.22 |
| Isopimaric acid % | 18.64 |
| Pimaric acid % | 5.41 |
| Neoabietic acid % | 16.40 |

TABLE 3

Characteristics of extracted terpenes

| Characteristic | Value |
|---|---|
| Acid Index | 0.27 |
| Alpha colour | 5 |
| Alpha pinene % | 66.63 |
| Camphene % | 1.53 |
| 3-Carene % | 15.88 |
| Beta pinene % | 0.54 |

Throughout the specification the aim has been to describe the preferred examples of the disclosure without limiting the disclosure to any one embodiment or specific collection of features. It will therefore be appreciated by those of skill in the art that, in light of the instant disclosure, various modifications and changes can be made in the particular examples exemplified without departing from the scope of the present disclosure.

All computer programs, algorithms, patent and scientific literature referred to herein is incorporated herein by reference.

The invention claimed is:

1. A method for extracting rosin and/or terpene fractions from a resinous wood, said method including the step of treating/contacting the resinous wood with an agent that comprises, consists or consists essentially of a terpene to thereby extract the rosin and/or terpene fractions from the resinous wood, wherein the rosin fraction:

has a Gardner colour number of no more than about 8;

is substantially free of contaminants;

has an acid value between about 160 to about 175; and comprises an abietic acid content in the range from about 15% to about 35%, about 15% to about 25% or about 15% to about 20% by weight thereof.

2. The method of claim 1, further including the initial step of at least partly subdividing or desizing the resinous wood.

3. The method of claim 2, wherein the period of time between the initial step of subdividing the resinous wood and treating the resinous wood with the agent is no more than about 8 weeks, no more than about 4 weeks or no more than about 2 weeks.

4. The method of claim 1, further including the step of separating the rosin fraction and the terpene fraction extracted from the resinous wood.

5. The method of claim 4, wherein separating the rosin fraction and the terpene fraction is performed at least in part by distillation to produce a distillate that comprises, consists essentially of or consists of the terpene fraction and a residual stream that comprises, consists essentially of or consists of the rosin fraction.

6. The method of claim 5, further including the step of separating the terpene fraction from the distillate.

7. The method of claim 1, further including the subsequent step of heating the resinous wood treated with the agent to at least partly remove residual portions of the agent and/or the terpene fraction therefrom.

8. The method of claim 1, wherein the step of treating the resinous wood with the agent is performed:

for a period of time from about 15 minutes to about 120 minutes;

at a temperature from about 75° C. to about 155° C.; and/or at a pressure of about 10 psi to about 75 psi.

9. The method of claim 1, wherein the resinous wood is treated in a counter-current/counter-flow manner with the agent.

10. The method of claim 1, wherein the terpene fraction comprises at least about 65%, at least about 70%, at least about 75% or at least about 80% pinenes by weight thereof.

11. The method of claim 1, wherein the terpene fraction: is substantially free of contaminants;

comprises less than about 20%, less than about 10%, less than about 5%, less than about 2.5% or less than about 1% terpene polymers by weight thereof;

and/or comprises less than about 10%, less than about 5%, less than about 2.5%, less than about 1% or less than about 0.5% synthetic pine oil by weight thereof.

12. The method of claim 1, wherein the terpene of the agent has, at least in part, been recovered, recycled or derived from a further terpene fraction previously extracted from a further resinous wood and/or the agent previously used to treat the further resinous wood.

13. The method of claim 1, wherein the resinous wood has been screened to remove portions thereof having a dimension of greater than 1 cm.

14. The method of claim 1, further including the step of screening the resinous wood to remove portions thereof having a dimension greater than 1 cm.

15. The method of claim 1, wherein the resinous wood has been screened to select for portions thereof having a dimension of between 0.3 cm and 0.6 cm.

16. The method of claim 1, further including the step of screening the resinous wood to select for portions thereof having a dimension of between 0.3 cm and 0.6 cm.

17. The method of claim 1, wherein the resinous wood consists of portions having a volume of between about 0.01 $cm^3$ and about 1 $cm^3$.

18. The method of claim 1, wherein the resinous wood consists of portions having a surface area of between about 0.03 $cm^2$ and about 0.5 $cm^2$.

19. The method of claim 1, wherein the terpene is present in the agent in an amount of at least 90% w/w of the agent.

20. The method of claim 1, wherein the terpene is present in the agent in an amount of between 95% to 100% w/w of the agent.

* * * * *